(12) United States Patent
Poelzing et al.

(10) Patent No.: US 11,020,426 B1
(45) Date of Patent: Jun. 1, 2021

(54) ELECTROLYTE FORMULATIONS AND USES THEREOF

(71) Applicant: VIRGINIA TECH INTELLECTUAL PROPERTIES, INC., Blacksburg, VA (US)

(72) Inventors: Steven Poelzing, Roanoke, VA (US); David Ryan King, Roanoke, VA (US)

(73) Assignee: VIRGINIA TECH INTELLECTUAL PROPERTIES, INC., Blacksburg, VA (US)

( * ) Notice: Subject to any disclaimer, the term of this patent is extended or adjusted under 35 U.S.C. 154(b) by 127 days.

(21) Appl. No.: 16/184,291

(22) Filed: Nov. 8, 2018

Related U.S. Application Data (60) Provisional application No. 62/583,216, filed on Nov. 8, 2017.

(51) Int. Cl.
| | |
|---|---|
| A61K 33/06 | (2006.01) |
| A61K 33/00 | (2006.01) |
| A61K 33/14 | (2006.01) |
| A61K 33/08 | (2006.01) |
| A61K 33/10 | (2006.01) |
| A61N 1/39 | (2006.01) |
| A61J 1/10 | (2006.01) |

(52) U.S. Cl.
CPC ............ *A61K 33/06* (2013.01); *A61K 33/00* (2013.01); *A61K 33/08* (2013.01); *A61K 33/10* (2013.01); *A61K 33/14* (2013.01); *A61J 1/10* (2013.01); *A61N 1/3904* (2017.08)

(58) Field of Classification Search
CPC ........ A61K 33/00; A61K 33/06; A61K 33/08; A61K 33/10; A61K 33/14; A61N 1/00

USPC ............................................................. 607/3
See application file for complete search history.

(56) References Cited

U.S. PATENT DOCUMENTS

| | | | | |
|---|---|---|---|---|
| 5,405,362 A | * | 4/1995 | Kramer ............... | A61M 5/1723 600/510 |
| 5,462,524 A | * | 10/1995 | Powell ................. | A61K 33/30 128/898 |
| 2012/0172781 A1 | * | 7/2012 | Wang ................. | A61M 1/3667 604/6.16 |

OTHER PUBLICATIONS

Wang et al. "The effects of calcium and sodium bicarbonate on severe hyperkalaemia during cardiopulmonary resuscitation: A retrospective cohort study of adult in-hospital cardiac arrest" Resuscitation 98. p. 105-111 (Year: 2016).*
Allen, D.G., et al., "The Effects of Low Sodium Solutions on Intracellular Calcium Concentration and Tension in Ferret Ventricular Muscle", J. Physiol., pp. 391-407.
Awad, Sherif et al., "The history of 0.9% saline", Clinical Nutrition, vol. No. 27, pp. 179-188, Accepted: Jan. 15, 2008.

(Continued)

*Primary Examiner* — Nathan J Jenness
(74) *Attorney, Agent, or Firm* — Carin R. Miller, Esq.; Johnson, Marcou, Isaacs & Nix, LLC (57) ABSTRACT

Described herein are low sodium formulations. In some embodiments, the low sodium formulations can contain an effective concentration of sodium and an effective concentration of calcium. The low sodium formulations can be provided as combination kit that can include, in some embodiments, a low sodium formulation and a defibrillation device. Also described herein are methods of administering the low sodium formulation to a subject in need thereof and performing cardiac resuscitation and/or defibrillation on the subject in need thereof.

19 Claims, 7 Drawing Sheets

(56) References Cited

OTHER PUBLICATIONS

Bay, Johannes et al., "Intracellular Na+ and cardiac metabolism", Journal of Molecular and Cellular Cardiology, vol. No. 61, pp. 20-27, Available online: May 28, 2013.

Berger, Stuart, "Survival From Out-of-Hospital Cardiac Arrest: Are We Beginning to See Progress?", Journal of the American Heart Association, vol. 6, No. 9, e007469, Accessed: Sep. 8, 2017.

Bers, D.M., "Cardiac excitation-contraction coupling", Nature, vol. 415, No. 6868, pp. 198-205, Jan. 10, 2002.

Brodie, T.G., et al., "On reflex cardiac inhibition", J Physiol., vol. 26 (1-2), pp. 92-106, Dec. 31, 1900.

Bunch, T.J., et al., "Trends in treated ventricular fibrillation out-of-hospital cardiac arrest: a 17-year population-based study", Heart Rhythm, vol. 1, No. 3, pp. 255-259, Sep. 2004.

Cherry, B.H., et al., "Pyruvate stabilizes electrocardiographic and hemodynamic function in pigs recovering from cardiac arrest", Experimental Biology and Medicine, vol. 240, pp. 1774-1784, Accepted: May 5, 2015.

Choi, H.J., et al., "Effect of cardiopulmonary resuscitation on restoration of myocardial ATP in prolonged ventricular fibrillation", Resuscitation, vol. 84, No. 1, pp. 108-113, Accepted: Jun. 1, 2012.

Curtis, M.J., et al., "Quantification of arrhythmias using scoring systems: An examination of seven scores in an in vivo model of regional myocardial ischaemia", Cardiovasc Research, vol. 22, No. 9, pp. 656-665, Accepted: Apr. 25, 1988.

Despa, Sanda, et al., "Na + transport in the normal and failing heart—Remember the balance", J Mol Cell Cardiol., vol. 61, pp. 2-10, Aug. 2013.

Elliott, A.C., et al., "Metabolic changes during ischaemia and their role in contractile failure in isolated ferret hearts", Journal of Physiology, vol. 454, pp. 467-490.

Entz, Michael, et al., "Heart Rate and Extracellular Sodium and Potassium Modulation of Gap Junction Mediated Conduction in Guinea Pigs", Frontiers in Physiology, vol. 7, Article 16, pp. 1-10, Feb. 2016.

Entz, Michael, et al., "Design and validation of a tissue bath 3D printed with PLA for optically mapping suspended whole heart preparations.", Am J Physiol—Hear Circ Physiol, vol. 313, pp. H1190-H1198, First Published: Sep. 22, 2017.

George S.A., et al., "Cardiac Conduction in Isolated Hearts of Genetically Modified Mice—Connexin43 and Salts", Prog Biophys Mol Biol., vol. 120 (1-3), pp. 189-198, Jan. 2016.

George S.A., et al., "Extracellular sodium dependence of the conduction velocity-calcium relationship: evidence of ephaptic self-attenuation", Am J Physiol Heart Circ Physiol., vol. 310, pp. H1129-H1139, First Published: Mar. 4, 2016.

George S.A., et al., "TNFα Modulates Cardiac Conduction by Altering Electrical Coupling between Myocytes", Frontiers in Physiology, vol. 8, Article 334, pp. 1-13, Published: May 23, 2017.

George S.A., et al., "Extracellular Sodium and Potassium Levels Modulate Cardiac Conduction in Mice Heterozygous Null for the Connexin43 Gene", Pflugers Arch., vol. 467, No. 11, pp. 2287-2297, Nov. 2015.

Greer-Short, Amara, et al., "Revealing the Concealed Nature of Long-QT Type 3 Syndrome. Circulation" Arrhythmia and Electrophysiology. vol. 10, No. 2, pp. 1-22, e004400, Feb. 2017.

Harguindey, Salvador, et al., Cariporide and other new and powerful NHE1 inhibitors as potentially selective anticancer drugs—an integral molecular/biochemical/ metabolic/clinical approach after one hundred years of cancer research, J Transl Med., vol. 11, No. 282, pp. 1-17, 2013.

Imahashi, Kenichi, et al., "Intracellular Sodium Accumulation During Ischemia as the Substrate for Reperfusion Injury", Circ Res., vol. 84, No. 12, pp. 1401-1406, Accepted: Apr. 9, 1999.

Iwai, Takeshi, et al., "Sodium accumulation during ischemia induces mitochondrial damage in perfused rat hearts", Cardiovascular Research, vol. No. 55, pp. 141-149, Accepted: Feb. 4, 2002.

Iwamoto Takahiro, et al., "Na+/Ca2+ Exchange Inhibitors: A New Class of Calcium Regulators", Cardiovascular & Haematological Disorders-Drug Targets, vol. 7, No. 3, pp. 188-198, 2007.

Koretsune, Yukihiro, et al., "Mechanism of ischemic contracture in ferret hearts: relative roles of [Ca2+]i elevation and ATP depletion", The American journal of physiology, vol. 258(1 Pt 2), pp. H9-H16, Jan. 1990.

Koretsune, Yukihiro, et al., "Mechanism of early ischemic contractile failure, Inexcitability, Metabolite Accumulation, or Vascular-Collapse?", Circulation Research, vol. 68, No. 1, pp. 255-262, Jan. 1991.

Kozeny G.A., et al., "In vivo effects of acute changes in osmolality and sodium concentration on myocardial contractility", Am Heart Journal, vol. 109, No. 2, pp. 290-296, Feb. 1985.

Lee, J.A., et al., "Mechanisms of acute ischemic contractile failure of the heart: Role of intracellular calcium", J Clin Invest., vol. 88, pp. 361-367, Aug. 1991.

Li, Heng, et al., "0.9% Saline Is Neither Normal nor Physiological", J Zhejiang Univ B., vol. 17, No. 3, pp. 181-187, Crosschecked: Feb. 15, 2016.

Lyon, A.R. et al., "Optical imaging of mitochondrial function uncovers actively propagating waves of mitochondrial membrane potential collapse across intact heart", J Mol Cell Cardiol., vol. 49, No. 4, pp. 565-575, Oct. 2010.

Maack,Christopher, et al., "Elevated cytosolic Na+ decreases mitochondrial Ca2+ uptake during excitation-contraction coupling and impairs energetic adaptation in cardiac myocytes", Circ Res., vol. 99, No. 2, pp. 172-182, Jul. 21, 2006.

Mozaffarian Dariush, "Heart Disease and Stroke Statistics—2015 Update a Report From the American Heart Association", Circulation, vol. 131, No. 4, pp. e29-322, Jan. 27, 2015.

Myerburg, R.J., et al., "Pulseless Electric Activity Definition, Causes, Mechanisms, Management, and Research Priorities for the Next Decade: Report From a National Heart, Lung, and Blood Institute Workshop", Circulation, vol. 128, No. 23, pp. 2532-2541, Dec. 2013.

Pott, Christian, et al. "Na+/Ca2+exchanger knockout mice: Plasticity of cardiac excitation-contraction coupling", Ann N Y Acad Sci., vol. 1099, No. 1, pp. 270-275, First Published: Apr. 13, 2007.

Teodorescu, Carmen, et al., "Factors Associated With Pulseless Electric Activity Versus Ventricular Fibrillation the Oregon Sudden Unexpected Death Study", Circulation, vol. 122, No. 21, pp. 2116-2122, Nov. 23, 2010.

Van Diepen, Sean, et al., "Multistate 5-Year Initiative to Improve Care for Out-of-Hospital Cardiac Arrest: Primary Results From the HeartRescue Project", J Am Heart Assoc., vol. 6, No. 9, pp. 1-17, e005716, 2017.

Veeraraghavan, Rengasayee, et al., "Interstitial volume modulates the conduction velocity-gap junction relationship", American journal of physiology, Heart and Circulatory Physiology, vol. 302, No. 1, pp. H278-286, Accepted in Final Form: Oct. 11, 2011.

Veeraraghavan, Rengasayee, et al., "Sodium channels in the Cx43 gap junction perinexus may constitute a cardiac ephapse: an experimental and modeling study", Pflugers Arch—Eur J Physiol, vol. 467, pp. 2093-2105, Publised online: Jan. 13, 2015.

Veeraraghavan, Rengasayee, et al., "Potassium Channels in the Cx43 Gap Junction Perinexus Modulate Ephaptic Coupling: An Experimental and Modeling Study", Pflugers Arch., vol. 468, No. 10, pp. 1651-1661, Oct. 2016.

Walker, Mja, et al., "The lambeth conventions: Guidelines for the study of arrhythmias in ischaemia, infarction, and reperfusion", Cardiovasc Res., vol. 22, No. 7, pp. 447-455, Accepted: Mar. 7, 1988.

Wang, Yigang, et al., "Mice With a Null Mutation in the NHE1 Na+H+Exchanger Are Resistant to Cardiac Ischemia-Reperfusion Injury", Circ Res., vol. 93, No. 8, pp. 776-782, Accepted: Aug. 28, 2003.

Wang, Lianguo et al., "Optical Mapping of Intra-Sarcoplasmic Reticulum Ca2+ and Transmembrane Potential in the Langendorff-perfused Rabbit Heart", Journal of Visualized Experiments, vol. 103, e53166, pp. 1-7, Sep. 10, 2015.

(56) References Cited

OTHER PUBLICATIONS

Weber, C.R., et al., "Dynamic Regulation of Sodium/Calcium Exchange Function in Human Heart Failure", Circulation, vol. 108, No. 18, pp. 2224-2229, Accepted: Nov. 4, 2003.
Williams, L.E., et al., "The Effect of Intravenous Lactated Ringer's Solution Versus 0.9% Sodium Chloride Solution on Serum Osmolality in Human Volunteers", Anesth Analg, vol. 88, pp. 999-1003, Accepted for Publication: Jan. 28, 1999.
Williams, Helen, et al., "Differences in the calcium-handling response of isolated rat and guinea-pig cardiomyocytes to metabolic inhibition: Implications for cell damage", Exp Physiol., vol. 85, No. 5, pp. 505-510, Accepted: Jul. 24, 2000.
Youngquist, Scott et al., "Beta-blocker use and the changing epidemiology of out-of-hospital cardiac arrest rhythms", Resuscitation, vol. 76, No. 3, pp. 376-380, Mar. 2008.
Feng, Niu Chun, et al., "A Selective Inhibitor of Na+/Ca+ Exchanger, SEA0400, Preserves Cardiac Function and High-Energy Phosphates against Ischemia/Reperfusion Injury", J Cardiovascular Pharmacology, vol. 47, No. 2, pp. 263-270, Feb. 2006.
Varma, Niraj et al., "Mechanisms underlying ischemic diastolic dysfunction: relation between rigor, calcium homeostasis, and relaxation rate", Am J Physiol Heart Cir Physiol. 284: H758-H771, Oct. 31, 2002.
Wang, J. et al., "SEA400, a Novel Na+/Ca+ Exchanger Inhibitor, Reduces Calcium Overload Induced by Ischemia and Reperfusion in Mouse Ventricular Myocytes" Physiol. Res. 56:17-23, 2007.
Rossi, G., et al., "Chronic Sodium Depletion Increases Myocardial Calcium Content in Normotensive Rats", The American Journal of the Medical Sciences, vol. 297, No. 3, pp. 153-157, Mar. 1989.

\* cited by examiner

ELECTROLYTE FORMULATIONS AND USES THEREOF

CROSS-REFERENCE TO RELATED APPLICATIONS

This application claims the benefit of and priority to U.S. Provisional Patent Application No. 62/583,216, filed on Nov. 8, 2017, entitled "Electrolyte Solution to Enhance Electrochemical Function," the contents of which is incorporated by reference herein in its entirety.

STATEMENT REGARDING FEDERALLY SPONSORED RESEARCH

This invention was made with Government support R01HL102298 awarded by the National Institutes of Health. The Government has certain rights in the invention.

BACKGROUND

More than 350,000 out-of-hospital sudden cardiac arrests (SCA) occur in the United States each year and have a high mortality rate. As such, there exists a need for compositions and methods to treat and/or prevent SCAs.

SUMMARY

Described herein are methods that can include the step(s) of administering a low sodium formulation to a subject in need thereof; and performing cardiac resuscitation, cardiac pacemaking, defibrillation, cardiac resuscitation and defibrillation, cardiac resuscitation and cardiac pacemaking, or defibrillation and cardiac pacemaking on the subject in need thereof,
wherein the low sodium formulation can include a concentration of sodium and wherein the concentration of sodium is 145 mM or less, and wherein the low sodium formulation can include a concentration of calcium and wherein the concentration of calcium ranges from about 1.5 mM to about 3.5 mM. The concentration of sodium can range from 145 mM to 77 mM. In some embodiments, the low sodium formulation does not contain potassium. The low sodium formulation can further include a counter anion. The counter anion can be chloride, bicarbonate, or hydroxide.

Also described herein are methods of treating and/or preventing electromechanical dissociation in a subject in need thereof that can include the step(s) of administering a low sodium formulation to the subject in need thereof; and performing cardiac pacemaking, defibrillation, cardiac resuscitation and defibrillation, cardiac resuscitation and cardiac pacemaking, or defibrillation and cardiac pacemaking on the subject in need thereof, wherein the low sodium formulation can include an effective concentration of sodium and wherein the effective concentration of sodium can be 145 mM or less, and wherein the low sodium formulation can include an effective concentration of calcium can range from about 1.5 mM to about 3.5 mM. The concentration of sodium can range from 145 mM to 77 mM. In some embodiments, the low sodium formulation does not contain potassium. The low sodium formulation can further include a counter anion. The counter anion can be chloride, bicarbonate, or hydroxide. The low sodium formulation can be delivered as rapidly as possible. The subject in need thereof can have or can be suspected of having spontaneous cardiac arrest. The subject in need thereof can have or can be suspected of having pulseless electrical activity.

Also described herein are kits that can include a low sodium formulation; and a defibrillation device, a cardiac resuscitation device, or a cardiac pacemaking device, wherein the low sodium formulation comprises an effective concentration of sodium and an effective concentration of calcium, wherein the effective concentration of sodium can be 145 mM or less and the effective concentration of calcium can range from about 1.5 mM to about 3.5 mM. The concentration of sodium can range from 145 mM to 77 mM. In some embodiments, the low sodium formulation does not contain potassium. The low sodium formulation can further include a counter anion. The counter anion can be chloride, bicarbonate, or hydroxide. The low sodium formulation can be contained in an intravenous fluid bag. The defibrillation device can be an external defibrillation device.

BRIEF DESCRIPTION OF THE DRAWINGS

Further aspects of the present disclosure will be readily appreciated upon review of the detailed description of its various embodiments, described below, when taken in conjunction with the accompanying drawings.

FIGS. 1A-1B show graphs that can demonstrate that elevating sodium ion ($Na^+$) concentration in the perfusate can decrease left-ventricular developed pressure (LVDP) at baseline.

FIGS. 2A-2B show graphs that can demonstrate that elevating $Na^+$ in the perfusate prolongs time to LVDP collapse in early ischemia.

FIGS. 3A-3D show graphs that can demonstrate that elevating $Na^+$ can accelerate the onset of ischemic contracture.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used in the specification and the appended claims, the singular forms "a," "an," and "the" include plural referents unless the context clearly dictates otherwise.

As used herein, "about," "approximately," "substantially," and the like, when used in connection with a numerical variable, can generally refer to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

Embodiments of the present disclosure will employ, unless otherwise indicated, techniques of molecular biology, organic chemistry, biochemistry, physiology, cell biology, and the like, which are within the skill of the art. Such techniques are explained fully in the literature.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible unless the context clearly dictates otherwise.

Definitions

As used herein, "administering" can refer to an administration that is oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration also includes delivery via pumps, implanted or external, and implanted time release capsules, e.g. subcutaneous or parenteral.

The term "biocompatible", as used herein, refers to a material that along with any metabolites or degradation products thereof that are generally non-toxic to the recipient and do not cause any significant adverse effects to the recipient. Generally speaking, biocompatible materials are materials that do not elicit a significant inflammatory or immune response when administered to a patient.

As used herein, "dose," "unit dose," or "dosage" refers to physically discrete units suitable for use in a subject, each unit containing a predetermined quantity of the low sodium formulation calculated to produce the desired response or responses in association with its administration.

As used herein, "effective amount" refers to the amount of a compound provided herein that is sufficient to effect beneficial or desired biological, emotional, medical, or clinical response of a cell, tissue, system, animal, or human. An effective amount can be administered in one or more administrations, applications, or dosages. The term cam also include within its scope amounts effective to enhance or restore to substantially normal physiological function. The "effective amount" can refer to the amount of a low sodium formulation described herein that, when administered to a subject in need thereof, can treat and/or prevent cardiac muscle electromechanical dissociation (EMD), sudden cardiac arrest, and/or pulseless electrical activity (PEA) in cardiac muscle or a symptom thereof.

As used herein, "effective concentration" refers to the concentration of one or more components that alone or in combination with another component can result in a specific or desired effect. The effective concentration can be the concentration of one or more components alone or in combination that can treat and/or prevent cardiac muscle electromechanical dissociation (EMD), sudden cardiac arrest, and/or pulseless electrical activity (PEA) in cardiac muscle or a symptom thereof. The effective concentration can be the concentration of sodium and/or calcium that can that can treat and/or prevent cardiac muscle electromechanical dissociation (EMD), sudden cardiac arrest, and/or pulseless electrical activity (PEA) in cardiac muscle or a symptom thereof.

As used herein, "organism", "host", and "subject" refers to any living entity comprised of at least one cell. A living organism can be as simple as, for example, a single isolated eukaryotic cell or cultured cell or cell line, or as complex as a mammal, including a human being, and animals (e.g., vertebrates, amphibians, fish, mammals, e.g., cats, dogs, horses, pigs, cows, sheep, rodents, rabbits, squirrels, bears, primates (e.g., chimpanzees, gorillas, and humans).

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" can refer to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" can refer to any acid or base addition salt whose counter-ions are non-toxic to the subject to which they are administered in pharmaceutical doses of the salts.

As used herein, "synergistic effect," "synergism," or "synergy" can refer to an effect arising between two or more molecules, compounds, substances, factors, or compositions that that is greater than or different from the sum of their individual effects.

As used herein, "therapeutic" can refer to treating, healing, and/or ameliorating a disease, disorder, condition, or side effect, or to decreasing in the rate of advancement of a disease, disorder, condition, or side effect. A "therapeutically effective amount" can therefore refer to an amount of a compound that can yield a therapeutic effect.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as cardiac EMD, SCA, and/or cardiac PEA. The effect can be therapeutic in terms of a partial or complete cure of a disease, condition, symptom or adverse effect attributed to the disease, disorder, or condition. The term "treatment" as used herein covers any treatment of cardiac EMD, SCA, and/or cardiac PEA. in a subject, particularly a human cardiac EMD, SCA, and/or cardiac PEA, and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain Discussion According to the American Heart Association's 2015 report, more than 350,000 out-of-hospital sudden cardiac arrests (SCA) occur in the United States each year. These SCA's have about a 90% mortality rate. Survival rates are more dependent on the presenting cardiac rhythms in SCA. A presenting cardiac rhythm with a poor prognosis is termed Pulseless Electrical Activity (PEA). PEA is a condition that often occurs after a cardiac arrest (e.g. SCA) or after defibrillatory shock to terminate a cardiac arrhythmia. About one third of SCA's are associated with PEA. The clinical presentation of PEA is complete electromechanical dissociation (EMD) in which there is a return of coordinated electrical activity of the cardiac muscle without restoration of physical muscle contraction resulting in a weak or absent pulse. There is no current treatment for post arrest PEA. At least in view of the high mortality rate and prevalence of PEA in the context of SCA's, there is a long-felt yet unmet need for treatments for this cardiac condition.

With that said, described herein are low sodium formulations and methods that can be used to treat and/or prevent PEA and/or EMD in the context of a cardiac arrest, such as an SCA. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Low Sodium Formulations

Treatment of SCA usually includes intravenous (IV) or intraosseous fluid therapy with 0.9% normal saline (NS) in conjunction with cardiopulmonary resuscitation. NS was designed in the late 1800's and is thought to maintain blood pressure by its hyperosmotic nature. However, despite the nomenclature "normal saline," the sodium concentration ($[Na]^+$) in NS is 155 mM is outside of the normal physiological range for humans, which ranges from about 135 mM to about 147 mM. Further the NS formulation has remained unchanged since its conception. It can be thought that venous introduction of high $[Na^+]$ solutions, like NS, may have an insubstantial effect on blood $[Na^+]$ as the solution would become rapidly diluted in the larger body of fluid; however it was recently demonstrated that administration of NS can significantly alter blood $[Na^+]$ levels. By administering NS in response to an SCA as is typically done, first responders (e.g. paramedics, emergency medical services, etc.) are introducing a pathologically high $[Na^+]$ into SCA patients during resuscitation attempts and creating a hypernatremic environment for cardiac cells. Without being bound by theory, administration of a NS or other formulation with high sodium concentration (e.g. greater than 145 mM) can exacerbate contractile and/or mitochondrial dysfunction in an ischemic heart and therefore exacerbate PEA and contribute to mortality associated with SCA and/or PEA. This effect can be mediated by the direct and/or indirect effects of Na+ mediated depolarization on intracellular calcium concentration.

Described herein are low sodium formulations that can be used to treat and/or prevent cardiac electromechanical dysfunction, such as that associated with SCA and/or PEA, and/or restore contractile function in the presence of electromechanical dysfunction. The low sodium formulation can contain an amount of water, sodium, calcium, and a counter anion. In some embodiments, the low sodium formulation does not include potassium. The low sodium formulation can be a pharmaceutical formulation.

The low sodium formulation can be a physiologically compatible composition that contains an effective concentration of sodium. The effective concentration of sodium can be 145 mM or less sodium. In some embodiments, the effective concentration of sodium can range from about 77 mM to 145 mM, about 130 mM to 145 mM, about 142 mM to 15 mM, or about 77 mM to about 137 mM. In some embodiments, the low sodium formulation can contain about 77 mM, 78 mM, 79 mM, 80 mM, 81 mM, 82 mM, 83 mM, 84 mM, 85 mM, 86 mM, 87 mM, 88 mM, 89 mM, 90 mM, 91 mM, 92 mM, 93 mM, 94 mM, 95 mM, 96 mM, 97 mM, 98 mM, 99 mM, 100 mM, 101 mM, 102 mM, 103 mM, 104 mM, 105 mM, 106 mM, 107 mM, 108 mM, 109 mM, 110 mM, 111 mM, 112 mM, 113 mM, 114 mM, 115 mM, 116 mM, 117 mM, 118 mM, 119 mM, 120 mM, 121 mM, 122 mM, 123 mM, 124 mM, 125 mM, 126 mM, 127 mM, 128 mM, 129 mM, 130 mM, 131 mM, 132 mM, 133 mM, 134 mM, 135 mM, 136 mM, 137 mM to about 138 mM, 139 mM, 140 mM, 141 mM, 142 mM, 143 mM, 144 mM, or 145 mM. In some embodiments, the concentration of sodium in the low sodium formulation can be about 77 mM, 78 mM, 79 mM, 80 mM, 81 mM, 82 mM, 83 mM, 84 mM, 85 mM, 86 mM, 87 mM, 88 mM, 89 mM, 90 mM, 91 mM, 92 mM, 93 mM, 94 mM, 95 mM, 96 mM, 97 mM, 98 mM, 99 mM, 100 mM, 101 mM, 102 mM, 103 mM, 104 mM, 105 mM, 106 mM, 107 mM, 108 mM, 109 mM, 110 mM, 111 mM, 112 mM, 113 mM, 114 mM, 115 mM, 116 mM, 117 mM, 118 mM, 119 mM, 120 mM, 121 mM, 122 mM, 123 mM, 124 mM, 125 mM, 126 mM, 127 mM, 128 mM, 129 mM, 130 mM, 131 mM, 132 mM, 133 mM, 134 mM, 135 mM, 136 mM, 137 mM, 138 mM, 139 mM, 140 mM, 141 mM, 142 mM, 143 mM, 144 mM, or about 145 mM.

The low sodium formulation can also contain calcium. The low sodium formulation can contain an effective concentration of calcium. The effective concentration of the calcium ($[Ca2+]$) can be 1.5 mM or greater. In some embodiments, the concentration of calcium can range from about 1.5 mM to 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.1 mM, 3.2 mM, 3.3 mM, 3.4 mM, to about 3.5 mM. In some embodiments, the effective concentration of the calcium in the low sodium formulation can be about 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.1 mM, 3.2 mM, 3.3 mM, 3.4 mM, or about 3.5 mM.

The low sodium formulation can contain a counter anion. Suitable counter anions can include, but are not limited to, acetate, aspartate, benzenesulfonate, benzoate, besylate, bicarbonate, bitartrate, bromide, camsylate, carbonate, chloride, citrate, decanoate, edetate, esylate, fumarate, gluceptate, gluconate, glutamate, glycolate, glycollylarsanilate, hexanoate, hydrabamine, hydroxide, hydroxynaphthoate, iodide, isethionate, lactate, lactobionate, malate, maleate, mandelate, mesylate, methylbromide, methylnitrate, methylsufate, mucate, napsylate, nitrate, octanoate, oleate, pamoate, phosphate, polygalacturonate, propionate, salicylate, stearate, subacetate, succinate, sulfate, tartrate, teoclate, tosylate, triethiiodide, and any permissible combination thereof. The suitable counter anion can be included at a suitable concentration ranging from about 1 mM to about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88. 89. 90. 91, 92, 93, 94, 95, 96, 97, 98, 99, 100, 101, 102, 103, 104, 104, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144 or 145 mM. One of ordinary skill in the art will understand that the concentration of the counter anion will depend on, inter alia, the concentration of the sodium, calcium, and type and/or concentration of the counter anion(s) and/or counter cation(s) included in the low sodium formulation. The counter anion can be biocompatible. The counter anion can be included in the form of a pharmaceutically acceptable salt.

The low sodium formulation can contain a counter cation that can be specific to the counter anion included in the low sodium formulation. Suitable counter cations can include aluminum, arginine, benzathine, chloroprocaine, potassium, choline, diethanolamine, ethanolamine, ethylenediamine, lysine, magnesium, histidine, lithium, meglumine, procaine, trimethylamine, zinc and any permissible combination thereof. The suitable counter cation can be included at a suitable concentration ranging from about 0 mM to about 1, 2, 3, 4, 5 mM. One of ordinary skill in the art will understand that the concentration of the counter cation will depend on, inter alia, the concentration of the sodium, calcium, and type and/or concentration of the counter cation and/or counter anion included in the low sodium formulation. The counter cation can be biocompatible. The counter cation can be included in the form of a pharmaceutically acceptable salt. In some embodiments, the low sodium formulation does not include a counter cation.

The low sodium formulation can contain additional ingredients such as dextrose, pyruvate, creatinine or any permissible combination thereof. In some embodiments the low sodium formulation can include epinephrine or be co-administered with epinephrine that is not contained in the low sodium formulation.

The low sodium formulation can be sterile. The low sodium formulation can be contained in any suitable container or packaging, including, but not limited to, a bottle, syringe, or intravenous fluid bag.

In some embodiments that low sodium formulation can include about 100 mM Na$^+$, about 102.5 mM Cl$^-$, and about 2.5 mM Ca$^{2+}$. In some embodiments that low sodium formulation can include about 129 mM Na$^+$, about 102 mM Cl$^-$, and about 3.0 mM Ca$^{2+}$. The low sodium formulations can also include water and additional counter anions such as lactate or hydroxide. In some embodiments, lactate, hydroxide, and/or other counter anions can be effective to raise pH.

Kits Containing a Low Sodium Formulation

The low sodium formulation described herein can be presented as a combination kit with one or more other pharmaceutical compounds or formulations and/or a defibrillation device. The defibrillation device can be any suitable defibrillation device. The defibrillation device can be an external defibrillator. The defibrillation device can be an internal defibrillator. As used herein, the terms "combination kit" or "kit of parts" refers to the compounds, or pharmaceutical formulations and additional components that are used to package, sell, market, deliver, and/or administer the combination of elements or a single element, such as the low sodium formulation described herein. Such additional components include, but are not limited to, packaging, syringes, tubing, catheters, needles, bottles, bags, wires, paddle electrodes, self-adhesive electrodes, and the like. Although the different components or elements of the kit can be packaged together, in some embodiments, a kit exists if one or more of the components or elements of the kits are presented together despite them being physically separate or separately packaged from one another. The low sodium formulation can be included in an intravenous fluid bag. The low sodium formulation can be sterile.

The kit can also include instructions printed on or otherwise contained in a tangible medium of expression. Instructions can be incorporated in labels, boxes, containers, syringes, delivery devices, defibrillator devices, insert sheets of paper, flash drives, CD-ROM, an internet website and the like. The instructions can provide information regarding the content of the compound or pharmaceutical formulations contained therein, safety information regarding the content of the low sodium formulations(s) or pharmaceutical formulation(s) contained therein, information regarding the dosages, indications for use, and/or recommended treatment regimen(s) for the low sodium formulation and/or pharmaceutical formulations contained therein.

In some embodiments, the instructions can include directions for administering the low sodium formulation to a subject having, or suspected of having, a SCA, EMD, PEA, myocardial ischemia and/or myocardial infarction. The instructions can include directions for administering the low sodium formulation to a subject having, or suspected of having, a SCA, EMD, PEA, myocardial ischemia and/or myocardial infarction before, during, and/or after performing cardiac resuscitation, cardiac pacemaking, and/or defibrillation. The instructions include directions for administering the low sodium formulation to the subject intravenously or intraosseously. In some embodiments, about 500 mL to about 1 L or about 2 L are administer to the subject. The low saline solution can be delivered via an electronic infusion pump or device, gravity (with or without clamp that can be regulated by a health care provider), and/or manually (e.g. a bag can be squeezed by a health care practitioner to increase the flow rate).

Uses of the Low Sodium Formulations and Kits Thereof

The low sodium formulations can be effective to treat and/or prevent SCA, EMD, PEA, myocardial ischemia and/or myocardial infarction in a subject in need thereof. The low sodium formulation can be administered before, during, and/or after cardiac resuscitation and/or defibrillation of the subject in need thereof. The low sodium formulation can be administered to the subject in need thereof via any suitable administration route, including but not limited to, intravenous, intraosseous, oral, subcutaneous. The low sodium formulation can be administered during non-surgical treatment. The low sodium formulation can be administered during a surgical procedure. During a surgical procedure it can be possible to directly deliver the low sodium formulation to the coronary arteries and cardiac tissue, such as via main lines and coronary catheterizations. The amount of the low sodium formulation administered to the subject in need thereof can vary. The amount of the low sodium formulation delivered can be dependent on, inter alia, the age, gender, weight, administration technique, and/or clinical presentation of the subject. In some embodiments, the amount administered can range from about 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 mL to about 525, 550, 575, 600, 625, 650, 675, 700, 725, 750, 775, 800, 825, 875, 900, 925, 950, 975, 1000, 1250, 1500, 1750, 2000, 2250, 2500, 2750, or 3000 mL or more. The amount administered can be about 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 875, 900, 925, 950, 975, 1000, 1250, 1500, 1750, 2000, 2250, 2500, 2750, or 3000 mL or more. The low sodium formulations can be delivered one or more times.

The delivery rate of the low sodium formulation can be varied. The delivery rate of the low sodium formulation can be dependent on, inter alia, the age, gender, weight, administration route, administration sight, and/or clinical presentation of the subject. Administration of the low sodium formulation can rapidly decrease the concentration of sodium and/or increase the calcium concentration in circulation of the subject in need thereof. Thus, administration of the low sodium formulation can decrease the extracellular concentration of sodium in the cardiac muscle. In some embodiments, the flow rate can be as rapidly as possible. The low saline solution can be delivered via an electronic infusion pump or device, gravity (with or without clamp that can be regulated by a health care provider), and/or manually (e.g. a bag can be squeezed by a health care practitioner to increase the flow rate).

The low sodium formulation can be administered before, during, and/or after cardiac resuscitation, cardiac pacemaking, and/or defibrillation of the subject in need thereof. Defibrillation can be administered by any suitable defibrillation device. Defibrillation can be manual or automatic. Defibrillation can be external or internal. Defibrillation devices and techniques will be appreciated by those of ordinary skill in the art. Cardiac pacemaking can be implemented by a cardiac pacemaker. The cardiac pace maker can be an internal or external pacemaker. Cardiac resuscitation, cardiac pacemaking, and/or defibrillation can be carried out, in some embodiments, via an automatic chest compression system.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure. The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Example 1

Figure 1A:
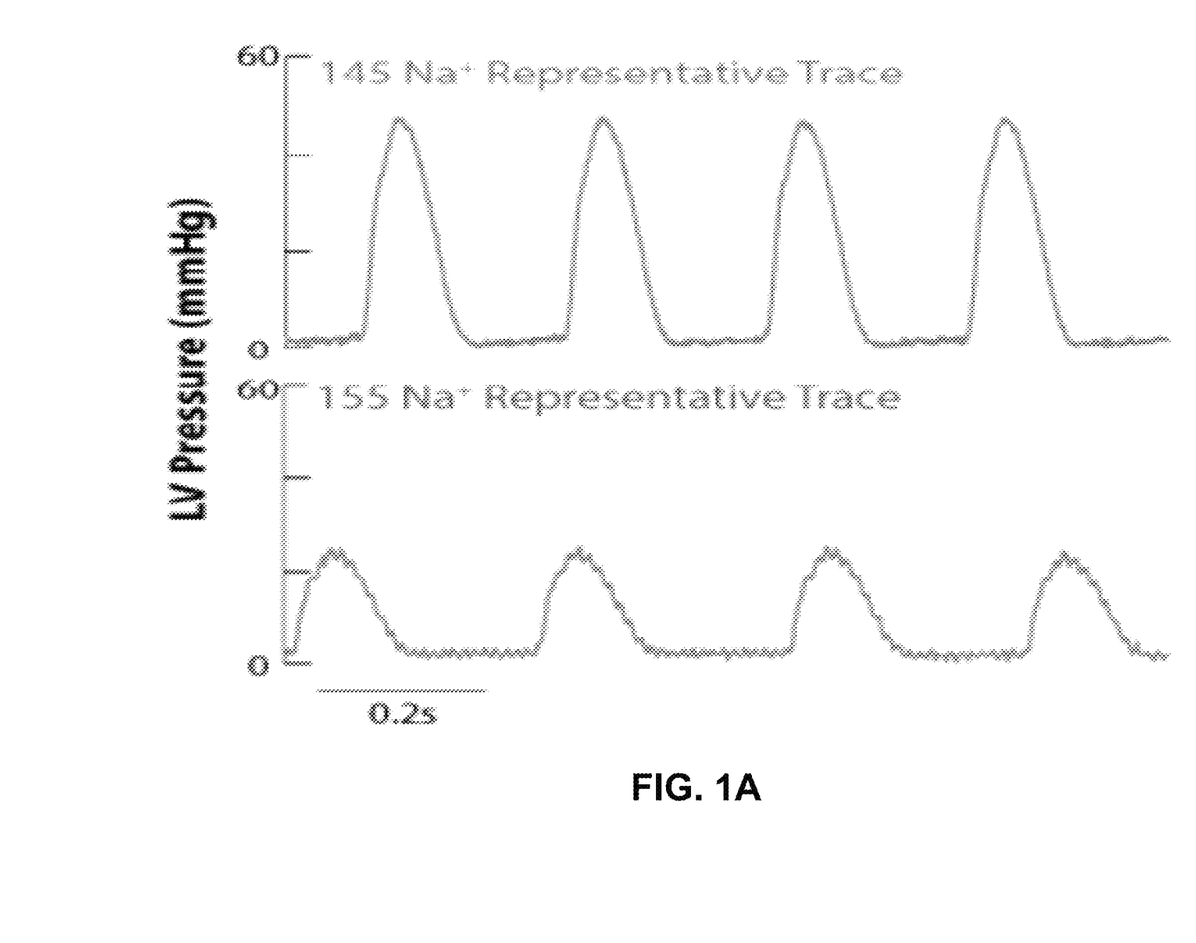
FIG. 1A shows representative traces of LVDP for 145 mM $Na^+$ and 155 mM $Na^+$ solutions.
Figure 1B:
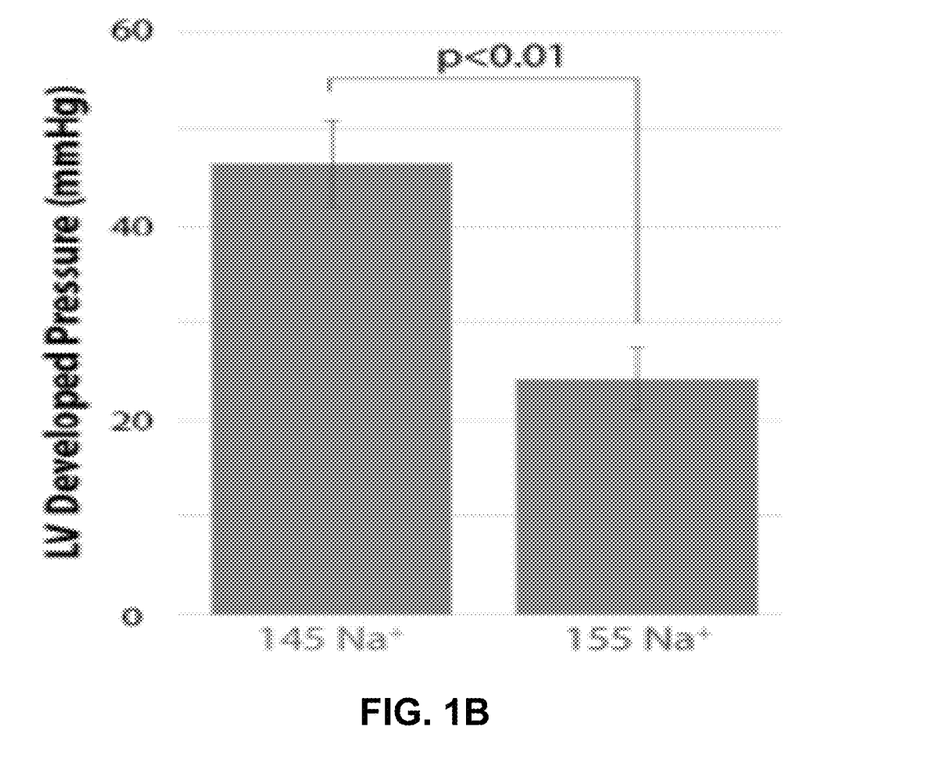
FIG. 1B shows a summary of LVDP at baseline (145 mM $Na^+$, n=10; 155 mM $Na^+$, n=10).

In this Example, perfusion of ex vivo isolated Sprague-Dawley rat hearts with bicarbonate buffered solutions of varying sodium concentrations ([$Na^+$], see Table 1) using the Langendorff technique. Hearts were suspended in a heated superfusion chamber at about 37° C. A volume-conducted electrocardiogram continuously measured electrical function throughout the experiments. All experiments were performed on a constant pressure (60 mmHg) Langendorff-apparatus. As can be demonstrated by FIGS. 1A-1B, at baseline (pre-ischemia), mechanical function, as assessed by left-ventricular developed pressure (LVDP; LVDP=systolic pressure–diastolic pressure for each contraction cycle) decreased when switching perfusate from the 145 mM $Na^+$ to the 155 mM $Na^+$ solution.

TABLE 1

Composition of bicarbonate buffered perfusates used in Example 1

| (in mM) | NaCl | NaHCO$_3$ | KCl | Dextrose | MgCl$_2$ | CaCl$_2$ |
|---|---|---|---|---|---|---|
| 145 mM $Na^+$ solution | 122.0 | 23.0 | 4.56 | 5.5 | 0.7 | 1.25 |
| 155 mM $Na^+$ solution | 132.0 | 23.0 | 4.56 | 5.5 | 0.7 | 1.25 |

In subsequent experiments, hearts were perfused with either the 145 mM $Na^+$ solution (n=10) or the 155 mM $Na^+$ solution (n=10). The hearts were cannulated and a size 4 isovolumetric pressure balloon was inserted in to the left ventricle. The hearts were allowed to stabilize for about 20 minutes prior to beginning data collection. In these experiments, LVDP was observed to be significantly lower in hearts perfused with the high sodium (155 mM $Na^+$) solution. See FIGS. 1A-1B. Neither heart rate nor flow rate varied significantly between the two groups.

Figure 2A:
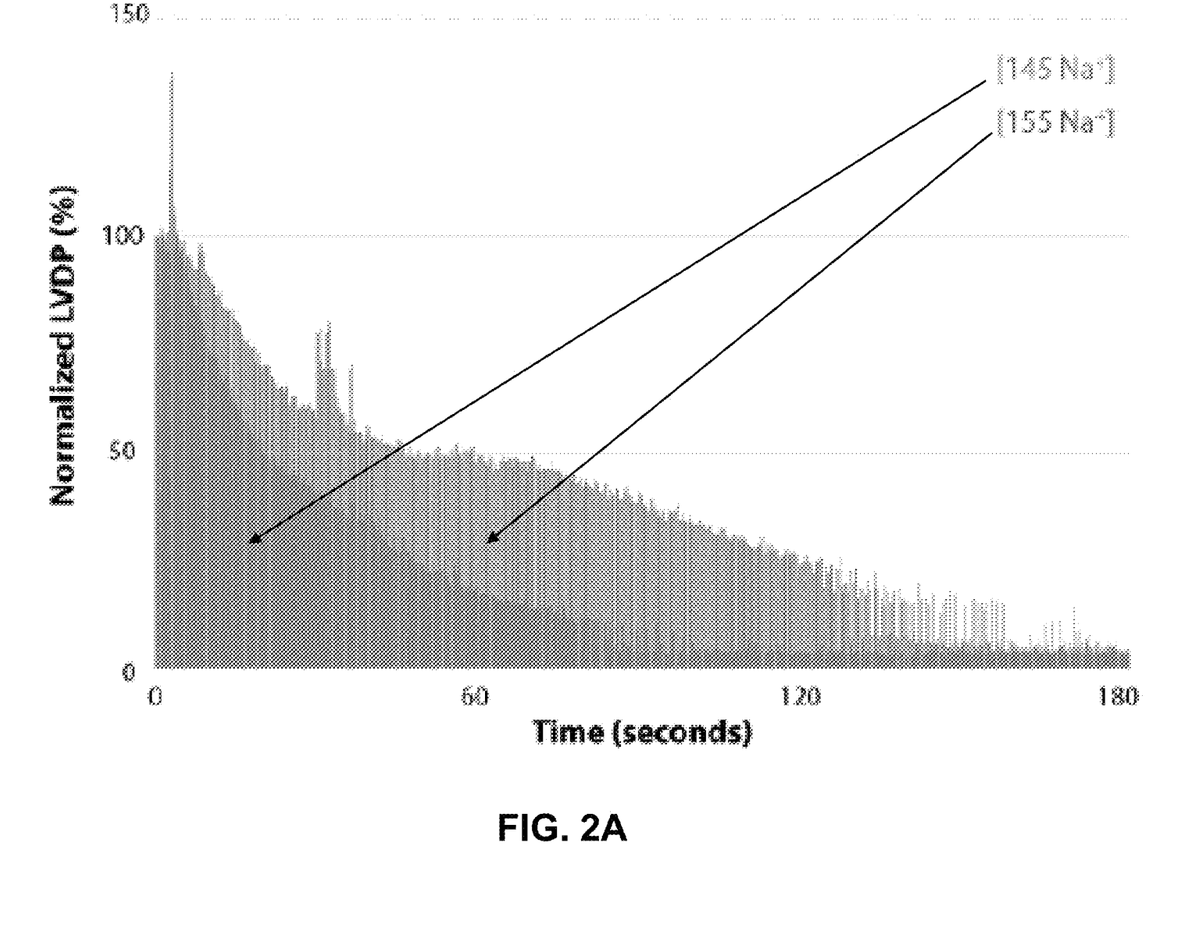
FIG. 2A shows an overlay of representative LVDP traces from hearts perfused with a 145 mM $Na^+$ or 155 mM $Na^+$ solution.
Figure 2B:
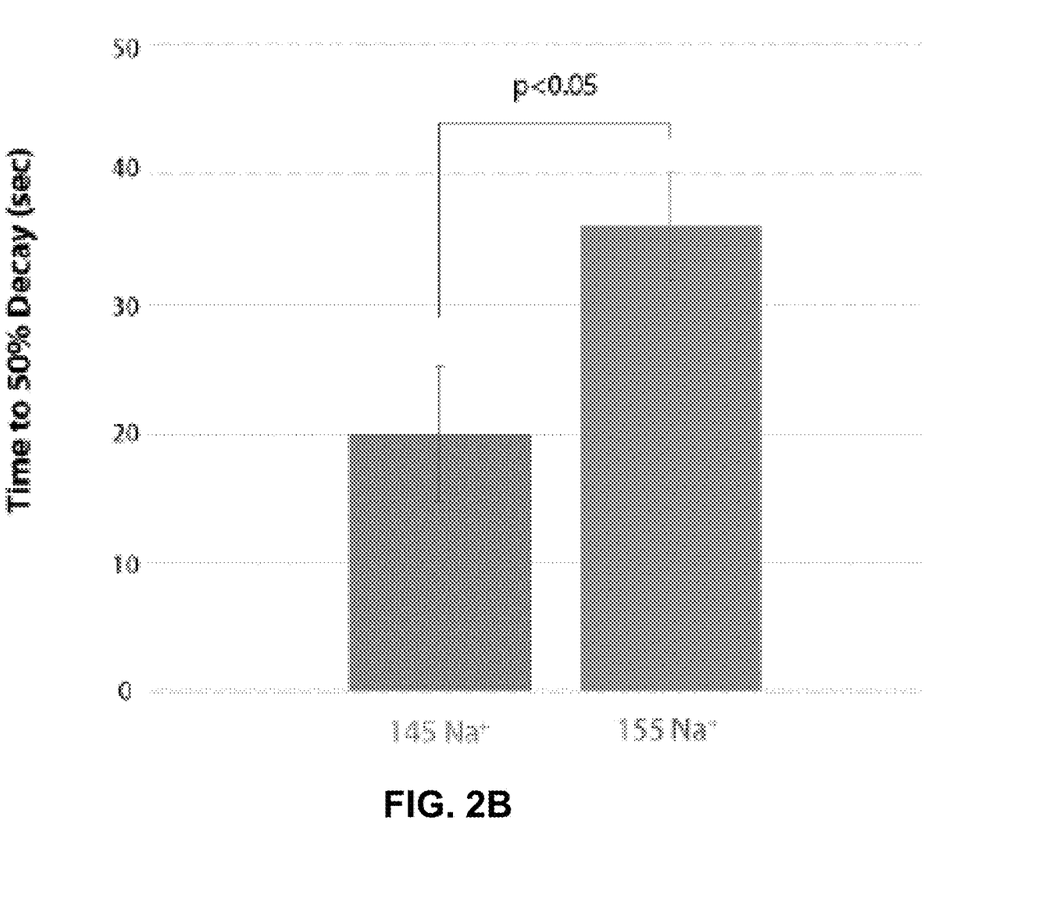
FIG. 2B shows the time to 50% LVDP decay for 145 mM $Na^+$ (n=8) and 155 mM $Na^+$ (n=8) solutions.

Following about 10 minutes of baseline data collection, global ischemia was induced by stopping the perfusate flow to the heart. Within minutes of stopping flow, LVDP collapsed and systole was lost. Unexpectedly, the time course of LVDP collapse in ischemia was observed to be solution dependent. See e.g. FIGS. 2A-2B. In these experiments, the hearts that were perfused with the high sodium (e.g. 155 mM $Na^+$) solution in the pre-ischemic period maintained systole longer into ischemia than hearts perfused with the low sodium (e.g. the 145 mM $Na^+$) solution. Intracellular acidosis can cause early ischemic contraction failure. Without being bound by theory, the high sodium solution can lead to intracellular acidosis by increasing the driving force on the cardiac $Na^+/H^+$ exchanger (NHE-1), in the $Na^+$-influx, $H^+$-efflux direction during early ischemia. This slows down intracellular proton accumulation during early ischemia and can delay systolic collapse.

Figure 3A:
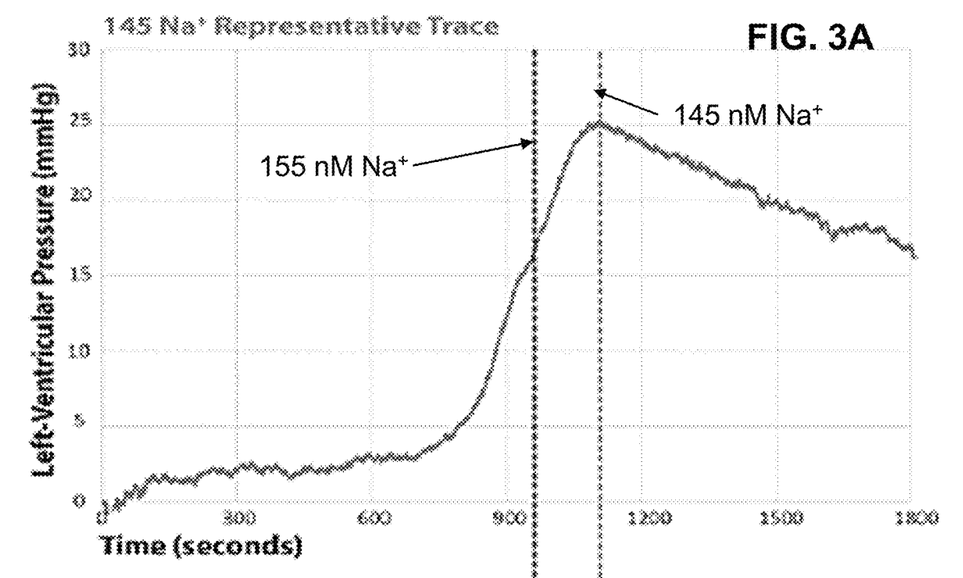
FIGS. 3A-3B show representative traces of Left-Ventricular Pressure following 145 mM $Na^+$ or 155 mM $Na^+$ perfusion, respectively. The dotted lines through the curve peaks are included for visualization.
Figure 3B:
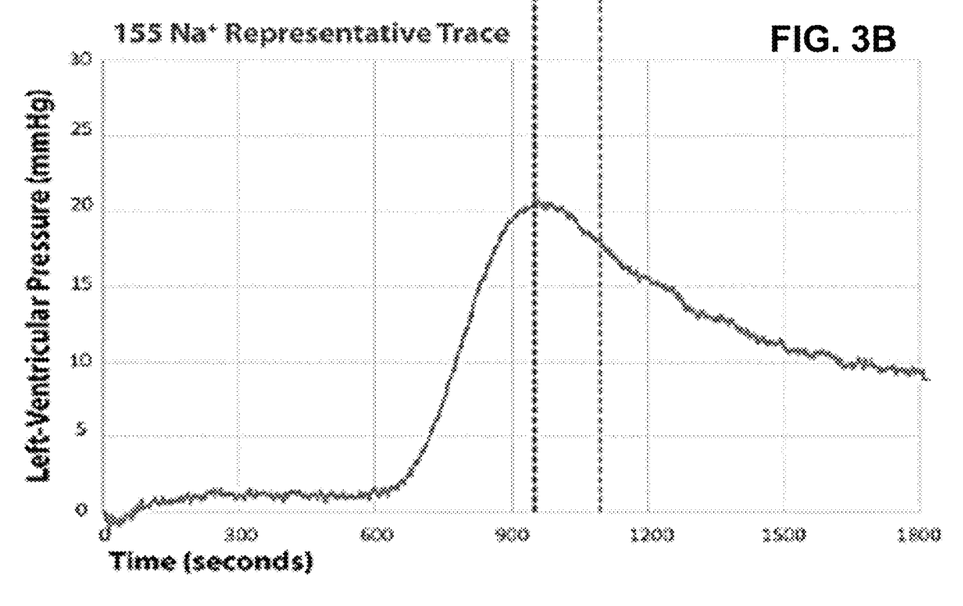
Figure 3C:
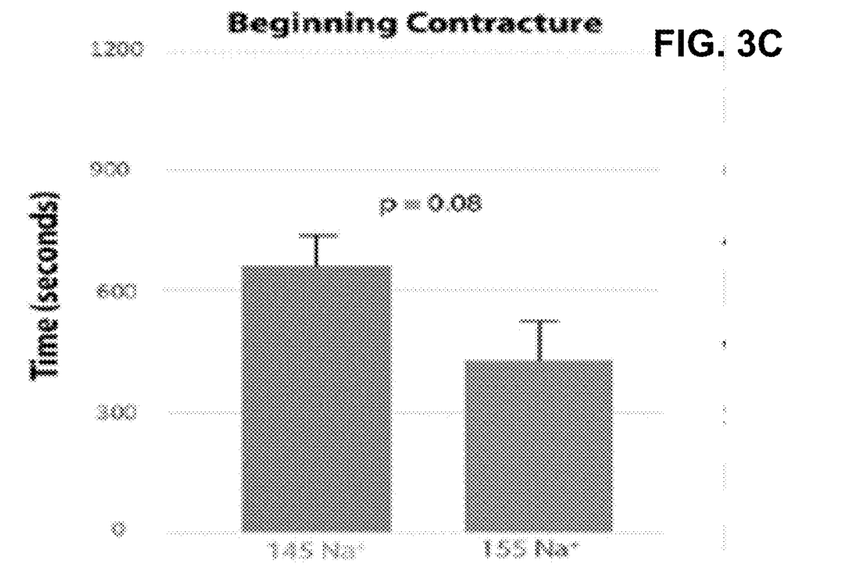
FIG. 3C shows a graph that can demonstrate the time to peak ischemic contracture.
Figure 3D:
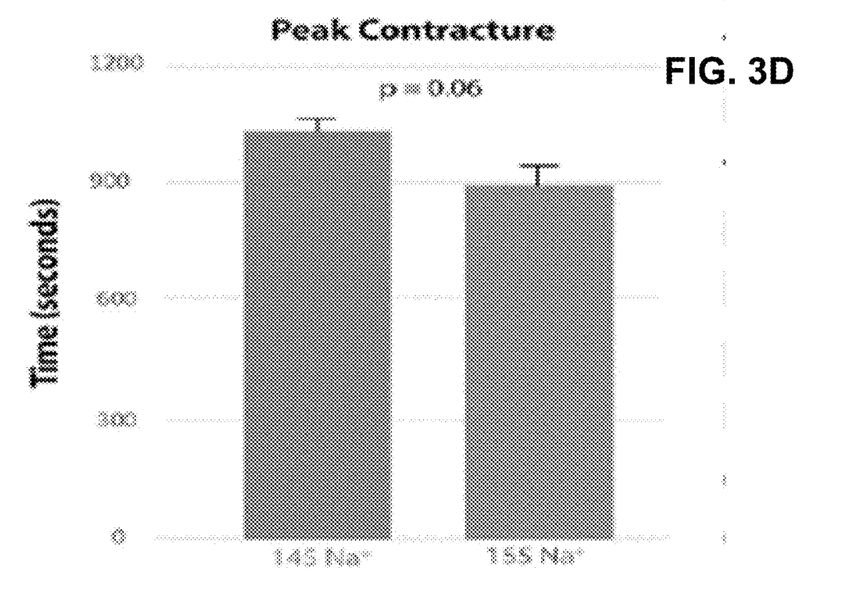
FIG. 3D shows a graph that can demonstrate the time to peak ischemic contracture (measured as time to maximum LV-pressure amplitude). (145 mM $Na^+$, n=7; 155 mM $Na^+$, n=8).

Following 8-10 minutes of ischemia, a sharp increase in left-ventricular diastolic tone (ischemic contracture). The onset of ischemic contracture is well correlated with the beginning of ATP depletion in the isolated hearts, and occurs later in species with more robust cytosolic glycogen stores (i.e. greater metabolic reserves). As compared with higher mammalian species, rats have small glycogen stores in cardiac tissue than other species. As such, ischemic contracture in rats begins in a period at which arrhythmia-free perfusion is still possible and can make rats a good, if not ideal, model for studying the effects of ischemic contracture on cardiac muscle post-ischemia. The time-course of ischemic contracture, as with LVDP collapse in early ischemia, appears to be perfusate dependent (See e.g. FIGS. 3A-3D). This data can support that 155 mM $Na^+$ perfusion can lead to an earlier onset of ischemic contracture (See e.g. FIGS. 3D-3C). Without being bound by theory, a delayed decay of LVDP at the beginning of ischemia (see FIGS. 2A-2B) can be attributable to increased $Na^+$-influx via NHE-1. Thus, a 155 mM $Na^+$ perfusion can result in accelerated intracellular $Na^+$ ($[Na^+]_i$) accumulation. Increased $[Na^+]_i$ can lead to impaired mitochondria function and decreased metabolic flexibility.

Figure 4:
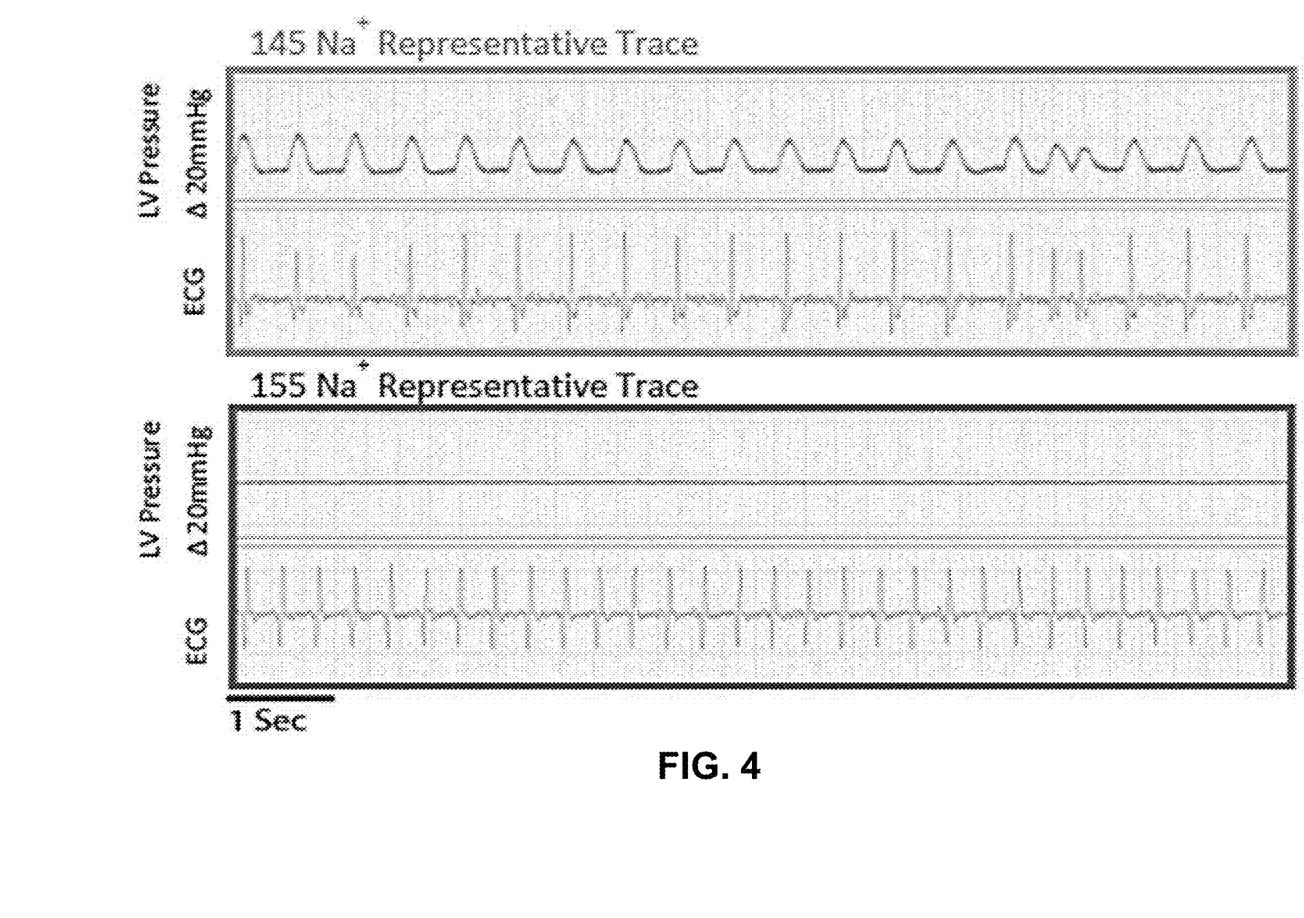
FIG. 4 show graphs that can demonstrate that elevating $Na^+$ can decrease left-ventricular developed pressure during reperfusion while still allowing for electrical activity of the heart. Top Traces shows representative left-ventricular developed pressure (LVDP) and electrical activity during cardiac reperfusion with 145 mM $Na^+$ following ischemia. Bottom Traces show that mechanical function (as quantified by LVDP) may not return but the ECG returns during cardiac reperfusion with 155 mM $Na^+$ following ischemia. This demonstrates electromechanical dissociation (EMD) also known as the more severe form pulseless electrical activity (PEA). (145 mM $Na^+$, n=7; 155 mM $Na^+$, n=8).

In further studies, reperfusion was started after about 10, about 30, and about 45 minutes of ischemia. Following about 10 minutes of ischemia the two experimental groups, 145 mM $Na^+$ (n=4) and 155 mM $Na^+$ (n=4) solutions, were similar in their functional recovery as assessed by ECG and return of LVDP. Following 45 minutes of ischemia, neither group (n=2 for both groups) regained organized electrical activity nor contractile rhythm. Following about 30 minutes of ischemia, hearts perfused with either the 145 mM $Na^+$ (n=7) or 155 mM ($Na^+$) (n=8) solution regained organized electrical activity about 50 percent of that time. In the 145 mM $Na^+$ group, hearts that recovered electrically had a return of LVDP to about 25 percent of baseline. In the 155 mM $Na^+$ group hearts that recovered electrically did not recovery mechanically. Instead these hearts presented with robust electromechanical dissociation (EMD). Clinical presentation of complete EMD, where there is a return of sinus rhythm and complete lack of contraction, as seen in FIG. 4, is termed Pulseless Electrical Activity (PEA). Thus, in addition, this Example can also demonstrate a model for PEA and that hypernatremia prior to, and in recovery from, an ischemic event can contribute and/or enhance PEA.

We claim:

1. A method comprising:
   administering a low sodium formulation to a subject in need thereof; and
   performing cardiac resuscitation, cardiac pacemaking, defibrillation, cardiac resuscitation and defibrillation, cardiac resuscitation and cardiac pacemaking, or defibrillation and cardiac pacemaking on the subject in need thereof,
      wherein the low sodium formulation comprises a concentration of sodium that ranges from 77 mM up to and less than 120 mM, and
      wherein the low sodium formulation comprises a concentration of calcium that ranges from about 1.5 mM to about 3.5 mM.

2. The method of claim 1, wherein the low sodium formulation does not contain potassium.

3. The method of claim 1, wherein the low sodium formulation further comprises a counter anion.

4. The method of claim 3, wherein the counter anion is chloride, bicarbonate, or hydroxide.

5. The method of claim 1, wherein the sodium concentration is 100 mM and the calcium concentration is 2.5 mM.

6. A method of treating and/or preventing electromechanical dissociation of cardiac muscle in a subject in need thereof, the method comprising:
   administering a low sodium formulation to the subject in need thereof; and
   performing cardiac pacemaking, defibrillation, cardiac resuscitation and defibrillation, cardiac resuscitation and cardiac pacemaking, or defibrillation and cardiac pacemaking on the subject in need thereof,
      wherein the low sodium formulation comprises an effective concentration of sodium that ranges from 145 mM to 77 mM, and
      wherein the low sodium formulation comprises an effective concentration of calcium that ranges from about 1.5 mM to about 3.5 mM.

7. The method of claim 6, wherein the low sodium formulation does not contain potassium.

8. The method of claim 6, wherein the low sodium formulation further comprises a counter anion.

9. The method of claim 8, wherein the counter anion is chloride, bicarbonate, or hydroxide.

10. The method of claim 6, wherein the low sodium formulation is delivered before, during, after, or any combination thereof, performing cardiac pacemaking, defibrillation, cardiac resuscitation and defibrillation, cardiac resuscitation and cardiac pacemaking, or defibrillation and cardiac pacemaking on the subject in need thereof.

11. The method of claim 6, wherein the subject in need thereof has or is suspected of having spontaneous cardiac arrest.

12. The method of claim 6, wherein the subject in need thereof has or is suspected of having pulseless electrical activity.

13. The method of claim 6, wherein the effective sodium concentration range is 77 mM up to and less than 120 mM.

14. A kit comprising:
   a low sodium formulation effective for treating, preventing, or treating and preventing electromechanical dissociation of cardiac muscle; and
   a defibrillation device or a cardiac pacemaking device,
   wherein the low sodium formulation comprises an effective concentration of sodium and an effective concentration of calcium,
   wherein the effective concentration of sodium ranges from 77 mM up to and less than 120 mM and the effective concentration of calcium ranges from about 1.5 mM to about 3.5 mM.

15. The kit of claim 14, wherein the low sodium formulation does not contain potassium.

16. The kit of claim 14, wherein the low sodium formulation further comprises a counter anion.

17. The kit of claim 14, wherein the low sodium formulation further comprises a counter anion and wherein the counter anion is chloride or bicarbonate.

18. The kit of claim 14, wherein the low sodium formulation is contained in an intravenous fluid bag.

19. The kit of claim 14, wherein the defibrillation device is an external defibrillation device.

* * * * *